(12) United States Patent
Yeh (10) Patent No.: US 7,988,708 B2
(45) Date of Patent: Aug. 2, 2011

(54) INTERSPINOUS PROCESS DISTRACTION DEVICE

(75) Inventor: Chung-Chun Yeh, Taipei (TW)

(73) Assignee: Biomed Ltd., Apia, Oox ( * ) Notice: Subject to any disclaimer, the term of this patent is extended or adjusted under 35 U.S.C. 154(b) by 686 days.

(21) Appl. No.: 11/654,628

(22) Filed: Jan. 18, 2007

(65) Prior Publication Data

US 2008/0177271 A1    Jul. 24, 2008

(30) Foreign Application Priority Data

Apr. 7, 2006   (TW) ............................... 95112512 A (51) Int. Cl.
*A61B 17/70*   (2006.01)

(52) U.S. Cl. .......... 606/248; 606/249; 606/105; 606/90; 623/17.11; 623/17.16

(58) Field of Classification Search .......... 606/246–249, 606/250–253, 257, 60, 61, 150, 90; 623/17.11–17.16
See application file for complete search history.

(56) References Cited

U.S. PATENT DOCUMENTS 5,885,284 A * 3/1999 Errico et al. .................. 606/252

FOREIGN PATENT DOCUMENTS

| TW | 091208091 | 8/2003 |
|----|-----------|--------|
| TW | 091212198 | 9/2003 |
| TW | 091215377 | 10/2003 |
| TW | 091213154 | 11/2003 |
| TW | 091216805 | 3/2004 |
| TW | 093205661 | 1/2005 |

\* cited by examiner

*Primary Examiner* — Eduardo C Robert
*Assistant Examiner* — Christina Negrelli
(74) *Attorney, Agent, or Firm* — Chun-Ming Shih (57) ABSTRACT

An interspinous process distraction device includes a male distraction element and a female distraction element, which both have a clamping portion for fixedly pushing and rejecting the interspinous processes and also respectively have a first connecting portion and a second connecting portion connected at the other end of the clamping portion. Here, the first connecting portion and the second connecting portion are paired for blocking with each other so as to form the interspinous process distraction device capable of having an opposite rotation. Besides, through clamping two interspinous processes which stress the nerve by the male distraction element and the female distraction element and rotating them to oppositely rotate, the two interspinous processes can therefore be moved to be in alignment as the normal condition.

8 Claims, 7 Drawing Sheets

INTERSPINOUS PROCESS DISTRACTION DEVICE

FIELD OF THE INVENTION

The present invention is related to an interspinous process distraction device, and more particularly to an interspinous process distraction device which can reject two interspinous processes of vertebra and distract thereof through an opposite rotation therebetween so as to return the vertebra to a normal position.

BACKGROUND OF THE INVENTION

Except the vertebral injury caused from fracture, most traditional vertebral diseases are relating to the atrophy caused by pathological changes located between intervertebral disks, such that the intervetebal intervals become smaller which also cause intervertebral foramens (nerve foramens) between intervertebral joints narrowed, and thus, the spinal nerve root will be stressed to cause paralysis or pain.

Currently, the therapy manner for the above problem is to implement pedicle screw to pull apart the intervertebral interval, or to implement artificial intervertebral cage or spacer for filling the interval so as to increase thereof and also enlarge the nerve foramen. There already have many similar inventions for fixing the vertebra and normalizing the intervertebral interval through pulling. For example, R.O.C Patent Application No. 093205661 "spinal fixer structure" discloses a fixer utilizing a first shaft and a second shaft as a set to connect plural pedicle screws so as to be mutually connected and have a moving space. However, in this manner, the pedicle screw has to be implemented into the spine for fixation which obviously will destroy the spine so that it actually is dangerous and complicated. Another method is to implement the artificial intervertebral cage or spacer into the interval, as disclosed in R.O.C Patent Application No. 091215377 "A scarf supporting reposition device used for cervical vertebra", in which the device will be filled between the vertebras so as to distract thereof. However, identically, it also has some limitation and difficulty. There are many disclosures, such as R.O.C Patent Application No. 091216805, No. 091213154, No. 091212198, and No. 091208091, devoted to reduce the danger and complicity as correcting the vertebra, but it still lacks of a convenient, safe and structure simple vertebra correction device. The key for solving the above problem is how to expand the nerve foramen and release the stressed nerve root and simultaneously make the surgery simple and effective, so that if the interspinous process between the two adjacent vertebras can be directly distracted by a specific device, then the stress on the nerve root can be released so as to cure the paralysis or pain.

SUMMARY OF THE INVENTION

Therefore, in view of the complicity and destruction on the spine caused by the conventional disclosures, the object of the present invention is to provide an interspinous process distraction device which has a simple and stable structure and is also movable for exactly achieving the effects of support and fixation.

The present invention is related to an interspinous process distraction device including a male distraction element and a female distraction element, which both have a clamping portion for fixedly pushing and rejecting the interspinous processes and also respectively have a first connecting portion and a second connecting portion connected at the other end of the clamping portion. Here, the first connecting portion and the second connecting portion are paired for blocking with each other and also have a buffering space therebetween for allowing an opposite rotation, so that the male distraction element and the female distraction element can be connected to form the interspinous process distraction device. Besides, through clamping two interspinous processes which stress the nerve by the male distraction element and the female distraction element and rotating them to oppositely rotate, the two interspinous processes can therefore be moved, and then, when the included angle between the male distraction element and the female distraction element becomes 180°, the two interspinous processes may be in alignment as the normal condition, so that the nerve is no more stressed and also the spine can be fixed to release the uncomfortableness.

BRIEF DESCRIPTION OF THE DRAWINGS

The foregoing aspects and many of the attendant advantages of this invention will be more readily appreciated as the same becomes better understood by reference to the following detailed description, when taken in conjunction with the accompanying drawings, wherein.

DESCRIPTION OF THE PREFERRED EMBODIMENT

Figure 1A:
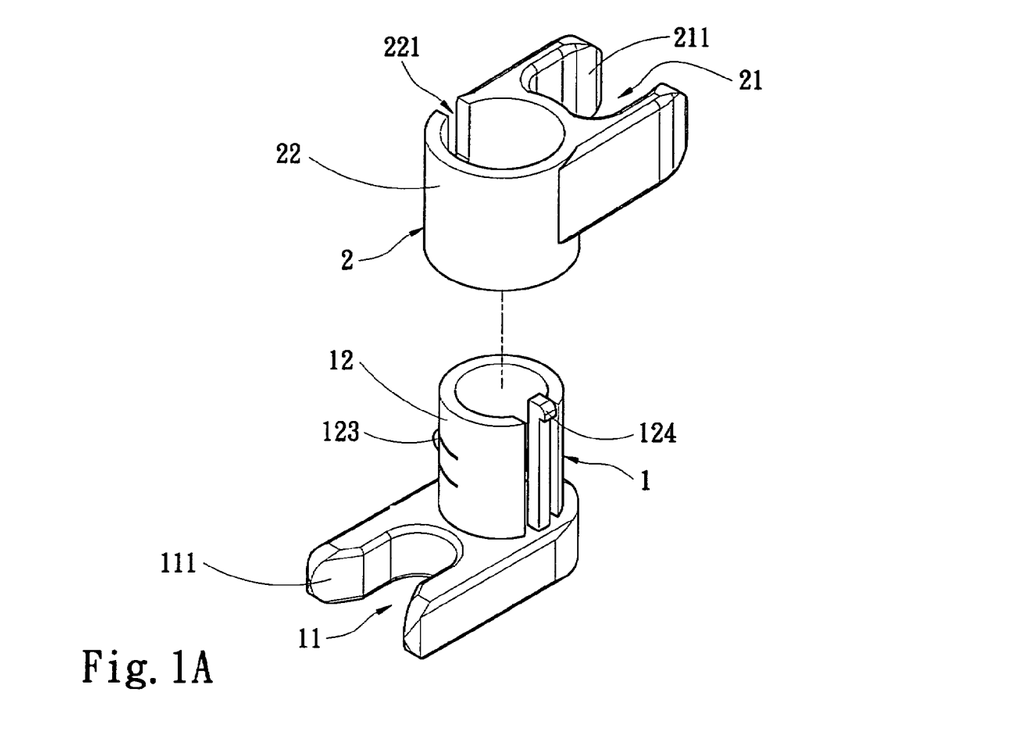
FIG. 1A is a decomposition drawing showing a first embodiment according to the present invention.
Figure 1B:
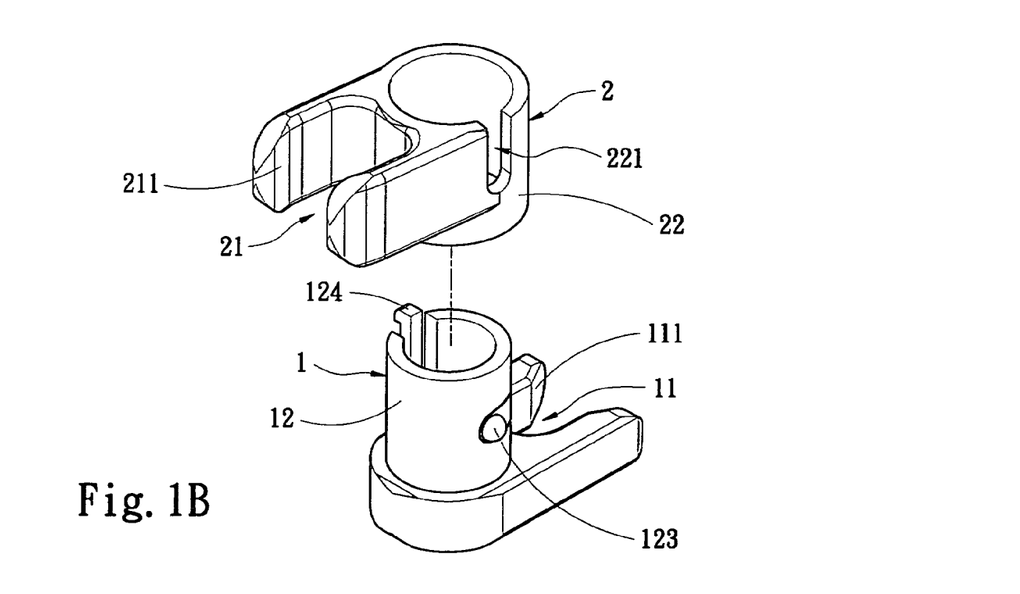
FIG. 1B is another decomposition drawing showing a first embodiment from another angle according to the present invention.
Figure 1C:
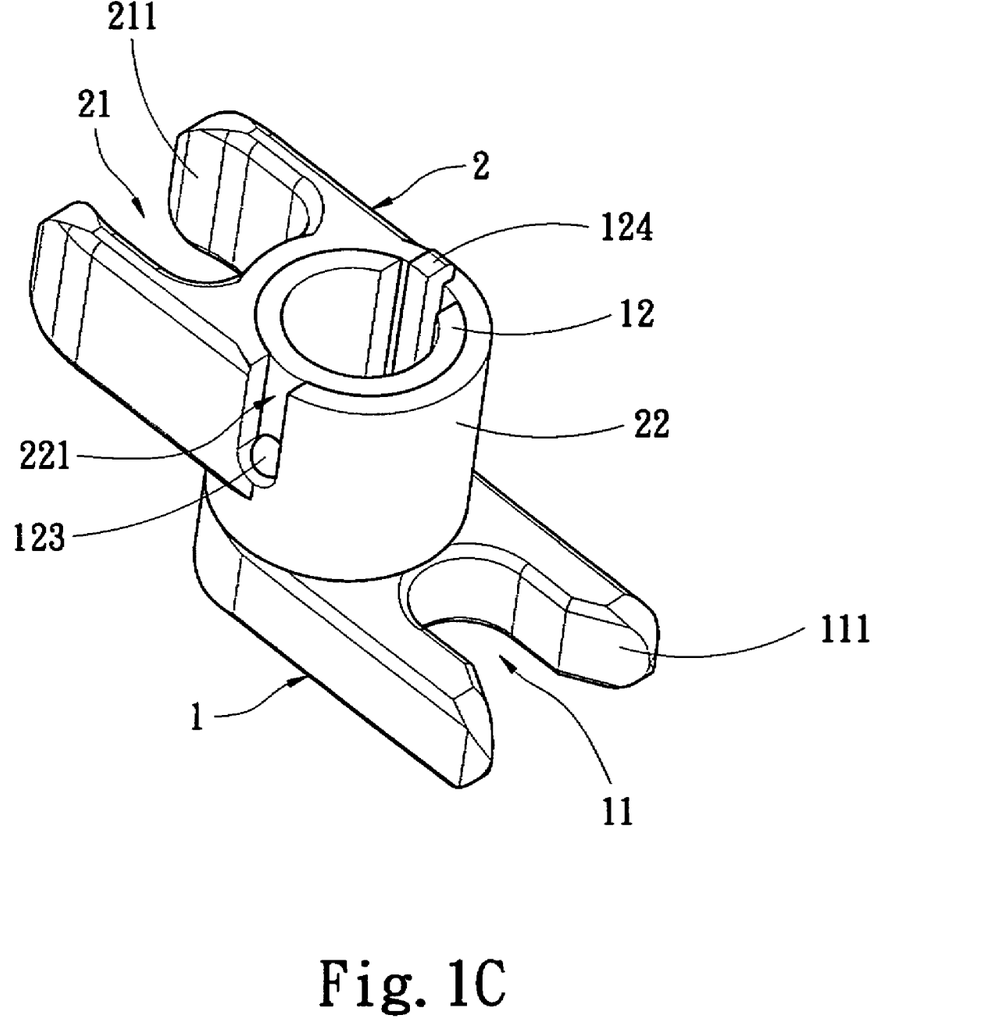
FIG. 1C is a three-dimensional assembling drawing showing a first embodiment according to the present invention.

Please refer to FIGS. 1A and 1B, which are the decomposition drawings showing a first embodiment of the present invention. The present invention is constituted by a male distraction element 1 and a female distraction element 2. The male distraction element 1 has a first clamping portion 11 and a first connecting portion 12, wherein the first clamping portion 11, connected at one end of the male distraction element 1, is constituted by two clamping arms 111 paired in a horizontal direction so as to form a space therebetween, and the first connecting portion 12, connected at the other end of the male distraction element 1, has an axle center extended therefrom and a first wedging element 123 and a second wedging element 124 mounted on the axle center, in which the first wedging element 123 is a flexible bulge and the second wedging element 124 is a pillar with a hook-like structure at the front end thereof. The female distraction element 2 has a second clamping portion 21 and a second connecting portion 22, wherein the second clamping portion 21, connected at one end of the female distraction element 2, is constituted by two clamping arms 211 paired in a horizontal direction so as to form a space therebetween, and the second connecting portion 22, connected at the other end of the female distraction element 2, has an axle space formed by a surrounding wall for being sleeved on the first connection portion 12 and has a limiting notch 221 mounted on the wall. The male distraction element 1 and the female distraction element 2 are connected together through assembling the first connecting portion 12 and the second connecting portion 22. When assembling, the axle center is sleeved by the axle space, and as sleeving, the first wedging element 123 on the axle center will inwardly shrink at first and then recover back in the limiting notch 221 of the female distraction element 2 if the first clamping portion 11 and the second clamping portion 21 have an included angle of 180°, so as to restrict the opposite rotation of the male and the female distraction elements 1 and 2 through limiting the lateral movement of first wedging element 123 by the limiting notch 221. Besides, the hook-like structure at the front end of the second wedging element 124 of the male distraction element 1 will lock at the top edge of the wall, which forms the axle space of the female distraction element 2, so as to restrict the vertical movement of the male and the female distraction elements 1 and 2. Please further refer to FIG. 1C, which shows the three-dimensional assembling drawing of the first embodiment. When the first clamping portion 11 and the second clamping portion 21 respectively of the male distraction element 1 and the female distraction element 2 have an included angle of 180°, the first wedging element 123 is fixed in the limiting notch 221 and the second wedging element 124 is hooked at the top edge of the wall surrounding the axle space of the female distraction element 2, so as to fix the male distraction element 1 and the female distraction element 2 together.

Figure 2A:
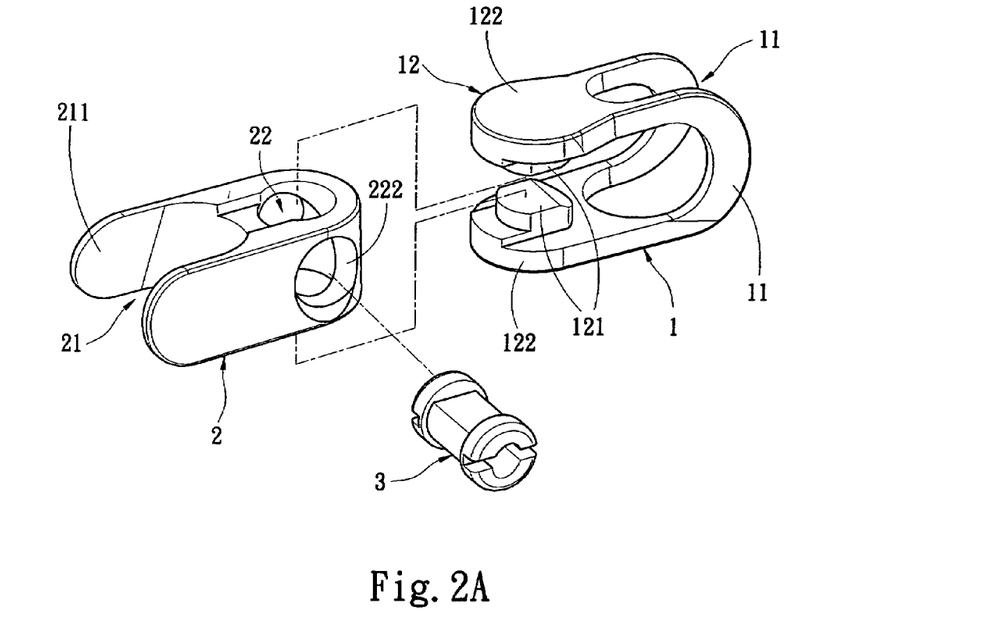
FIG. 2A is a decomposition drawing showing a second embodiment according to the present invention.
Figure 2B:
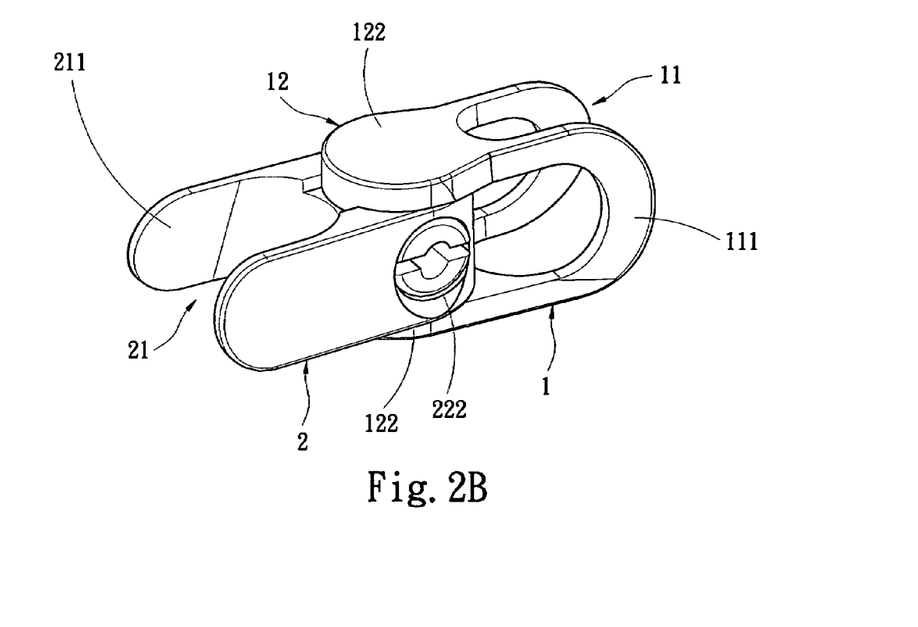
FIG. 2B is a three-dimensional drawing showing a second embodiment according to the present invention.

Please refer to FIGS. 2A and 2B, which are respectively a decomposition drawing and a three-dimensional assembling drawing showing a second embodiment according to the present invention. In this embodiment, the first clamping portion 11 and the first connecting portion 12 of the male distraction element 11 are formed to be a U shaped structure, wherein the first connecting portion 12 is formed by two connecting arms 122, aligned in a vertical direction, which respectively have a bulge, inwardly extended, at the opposite surfaces thereof, and at the left and right sides and the top side of the bulges, a fixing plane 121 is respectively mounted thereon, and the front and the rear ends of bulges remain the arc shape. The second connecting portion 22 of the female distraction element 2 has an axle hole 222 in the horizontal direction and the upper and lower ends of the second connecting portion 22 are respectively chiseled to have an indentation trough for combining with the bulges of the first connecting portion 12, so that the first connecting portion 12 will be operated as a damper to clamp on the second connecting portion 22. Moreover, a latch element 3 will pass through the axle hole 222 in a horizontal state, wherein the latch element 3 can be a pillar with two planes respectively at the top and the bottom, as in the horizontal state, of the middle section thereof, and the two planes can exactly match to the fixing plane 121 at the top of the first connecting portion 12, so that after the latch element 3 is plugged into the first connecting portion 12 and the second connecting portion 22, it can reject against the fixing planes 121 so as to fixedly connect the first connecting portion 12 with the second connecting portion 22. In addition, the latch element 3 further has grooves at two sides and a through hole which are used for moving and drawing out the latch element 3.

Figure 3:
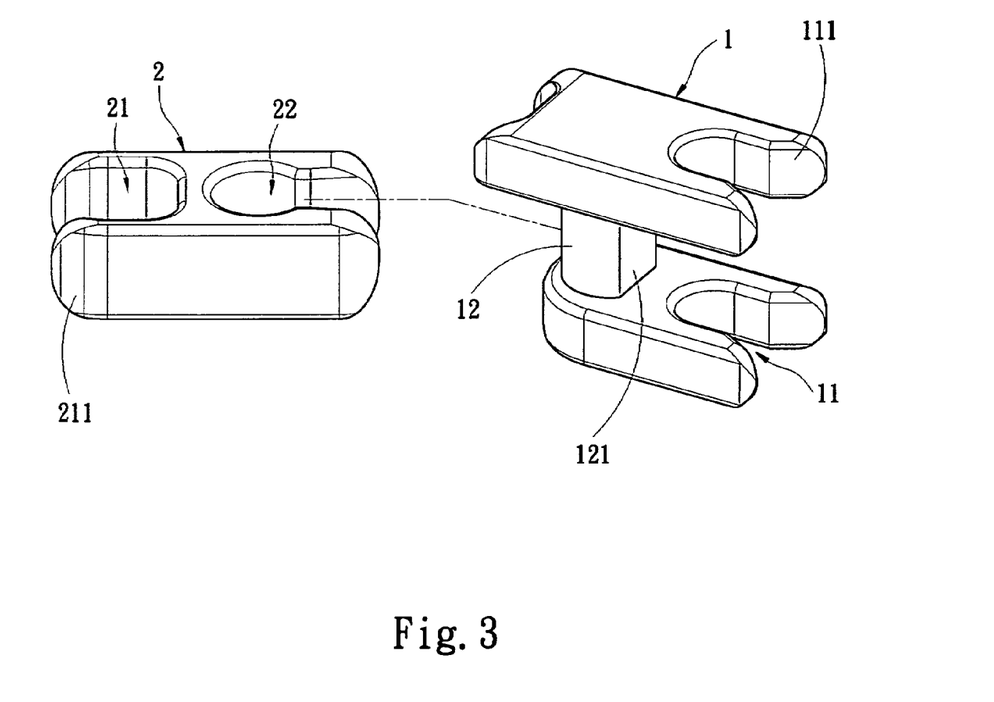
FIG. 3 is a decomposition drawing showing a third embodiment according to the present invention.

Please refer to FIG. 3 which shows the decomposition drawing of a third embodiment according to the present invention. In this embodiment, the first clamping portion 11 of the male distraction element 1 is separated into two levels which are connected together by the first connecting portion 12 to form a "U" shape. The first connecting portion 12 is a pillar connected between the first clamping portion 11, and the front and rear ends of the first connecting portion 12 have fixing planes 121 and other ports remain arc. Furthermore, the second connecting portion 22 of the female distraction element 2 is an inward trough whose opening is just for passing through the width between two fixing planes 121 on the first connecting portion 12. When the first clamping portion 11 and the second clamping portion 12 respectively of the male distraction element 1 and the female distraction portion 2 have an included angle of 180°, the arc edge of the first connecting portion 12 will be limited in the inward trough of the second connecting portion 22 so as to complete the assembling of the male distraction element 1 and the female distraction portion 2.

Figure 4A:
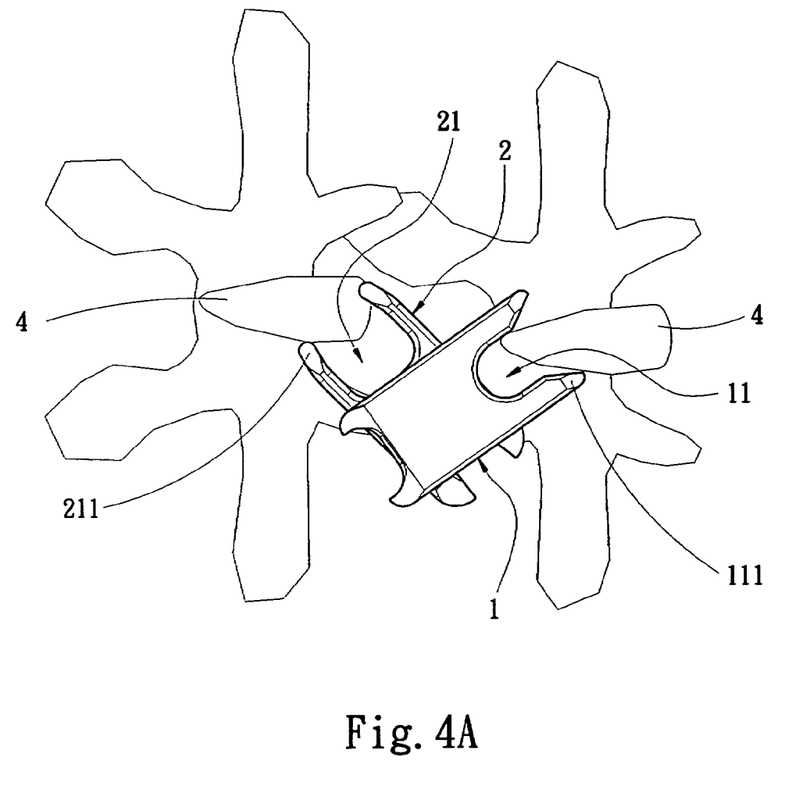
FIG. 4A is a schematic view showing the first application situation according to the present invention.
Figure 4B:
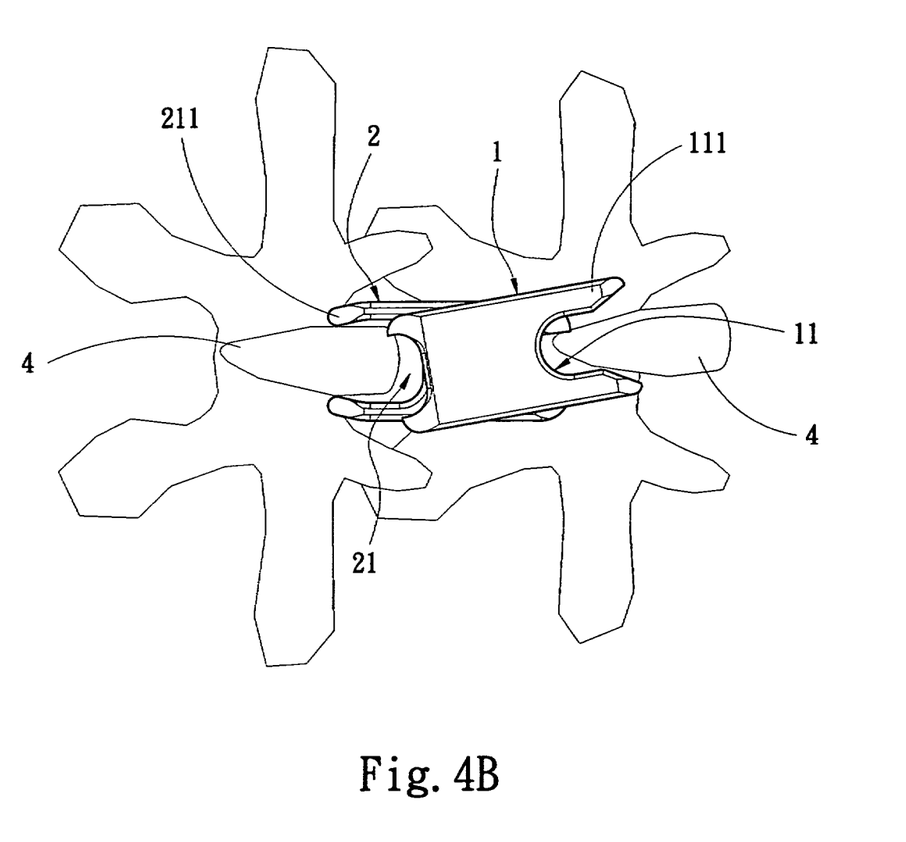
FIG. 4B is a schematic view showing the second application situation according to the present invention.
Figure 4C:
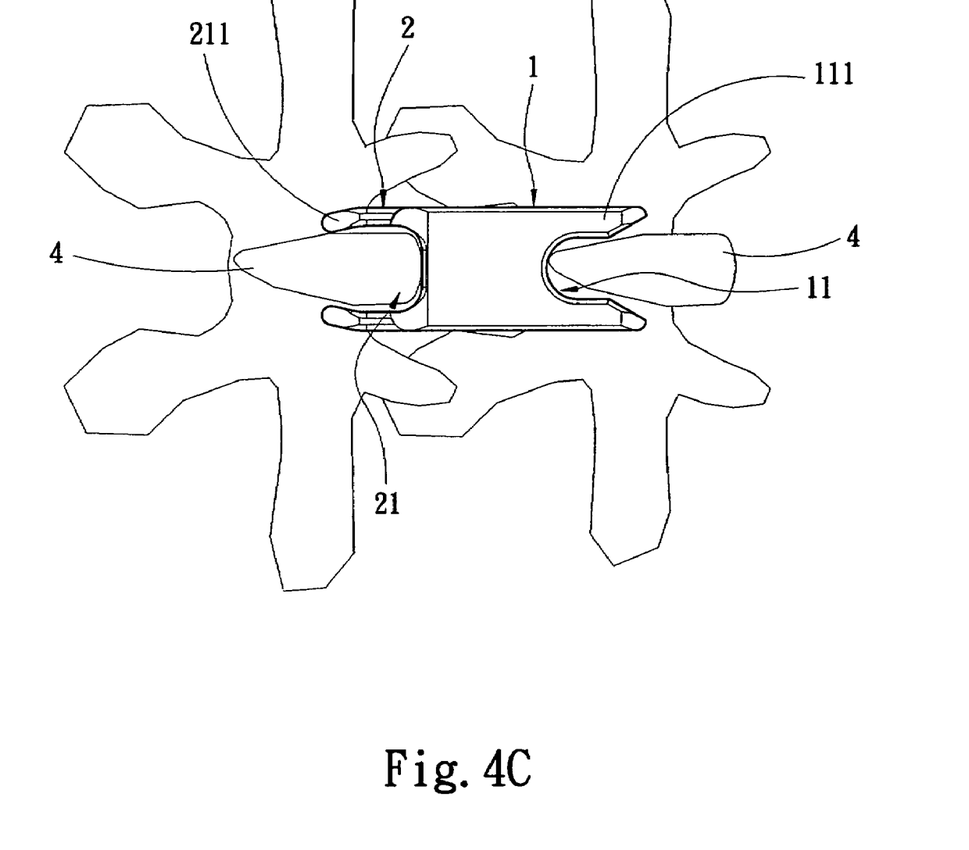
FIG. 4C is a schematic view showing the third application situation according to the present invention.

Please refer to FIGS. 4A to 4C, which are schematic views showing the practical application situations according to the present invention. After the male distraction element 1 and the female distraction portion 2 are connected, the first clamping portion 11 and the second clamping portion 21 will respectively reject on the interspinous processes 4 of two crooked vertebras, and then, the trough structures of the first clamping portion 11 and the second clamping portion 21 can accommodate the interspinous processes 4 for positioning. Moreover, the first clamping portion 11 and the second clamping portion 21 respectively of the male distraction element 1 and the female distraction portion 2 can be rotated to open until the included angle becomes 180°, so as to fix the interspinous processes 4 in alignment, and further, as the first clamping portion 11 and the second clamping portion 12 are rotated to have the included angle of 180°, they can be wedged and blocked, so that the interspinous processes 4 can be lastingly fixed at the normal position.

The advantages of the present invention are:
1. The structure is simple and the assembling is easy.
2. There is no need to implement the bone nail which obviously may destroy the bone.
3. The distraction device according to the present invention only needs to implement from one side of the spine which can reduce the cut and also the surgery difficulty.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:
1. An interspinous process distraction device for clamping and distracting an interspinous process and releasing a stressed nerve, comprising:
   a male distraction element having at least one first clamping portion receiving an interspinous process and a first connecting portion, wherein the first clamping portion and the first connecting portion are respectively connected at two ends of the male distraction element; and
   a female distraction element having a second clamping portion receiving an interspinous process and a second connecting portion, wherein the second clamping portion and the second connecting portion are respectively located at two ends of the female distraction element, and the second connecting portion is paired and mutually blocked with the first connecting portion and has a rotation space about an axis so that the male distraction device and the female distraction device own an opposite rotation function;

said axis extending perpendicular to a plane in which the first clamping portion lies;

wherein the first clamping portion of the male distraction element and the second clamping portion of the female distraction element respectively have a trough structure into each of which an interspinous process extends so as to clamp the interspinous process on the spine; and wherein the first clamping portion of the male distraction element and the second clamping portion of the female distraction element have an included angle of 180°, so as to fix the interspinous processes in alignment.

2. The interspinous process distraction device as claimed in claim 1, wherein the first connecting portion of the male distraction element has an axle center extended therefrom and a first wedging element and a second wedging element mounted on the axle center.

3. The interspinous process distraction device as claimed in claim 2, wherein the second connecting portion of the female distraction element has an axle space formed by a surrounding wall for being sleeved on the first connection portion, and has a limiting notch mounted on the wall for restricting the first wedging element, so that a rotation between the male distraction element and the female distraction element has a limited range.

4. The interspinous process distraction device as claimed in claim 3, wherein the second wedging element is locked at the edge of the wall surrounding the axle space.

5. The interspinous process distraction device as claimed in claim 1, further comprising a latch element for connecting and rotating the first connecting portion and the second connecting portion.

6. The interspinous process distraction device as claimed in claim 5, wherein the latch element is a pillar for fixedly connecting the first connecting portion with the second connecting portion and has two planes respectively at the top and the bottom, as in a horizontal state, of the middle section thereof.

7. The interspinous process distraction device as claimed in claim 1, wherein the first clamping portion of the male distraction element is separated into two levels which are connected together by the first connecting portion to form a "U" shape, and the first connecting portion is a pillar connected between the first clamping portion.

8. The interspinous process distraction device as claimed in claim 7, wherein the second connecting portion of the female distraction element is an inward trough capable of being blocked with the trough structure of the first connecting portion.

* * * * *